United States Patent [19]

Ziegler et al.

[11] Patent Number: 5,169,624

[45] Date of Patent: Dec. 8, 1992

[54] WATERPROOF SUNBLOCK COMPOSITIONS

[75] Inventors: Philip D. Ziegler, Oxford; Michael C. Cheney, Fairfield, both of Conn.

[73] Assignee: Chesebrough-Pond's USA Co., Division of Conopco, Inc., Greenwich, Conn.

[21] Appl. No.: 662,880

[22] Filed: Feb. 23, 1991

[51] Int. Cl.$^5$ .......................... A61K 7/40; A61K 7/42; A61K 7/44

[52] U.S. Cl. ........................................ 424/59; 424/60; 514/777; 514/938

[58] Field of Search .................................... 424/59, 60

[56] References Cited

U.S. PATENT DOCUMENTS

| | | | |
|---|---|---|---|
| 3,344,018 | 9/1967 | Shibe, Jr. et al. | 424/59 |
| 4,209,449 | 6/1980 | Mayhew et al. | 260/403 |
| 4,389,418 | 6/1983 | Burton | 514/938 |
| 4,438,095 | 3/1984 | Grollier et al. | 424/70 |
| 4,503,002 | 3/1985 | Mayhew et al. | 260/945 |
| 4,663,159 | 5/1987 | Brode, II et al. | 424/70 |
| 4,801,447 | 1/1989 | Gum | 424/68 |
| 4,886,890 | 12/1989 | Chaudhuri et al. | 548/519 |
| 4,897,259 | 1/1990 | Murray et al. | 514/938 |

OTHER PUBLICATIONS

Monaquat P Series Technical Bulletin, Jul., 1981.
Crodata Bulletin, Jun. 1986.

*Primary Examiner*—Dale R. Ore
*Attorney, Agent, or Firm*—Milton L. Honig

[57] ABSTRACT

A sunscreen composition is provided which includes from about 0.1 to about 30% by weight of a quaternary ammonium functionalized phosphate ester, from about 0.01 to about 10% by weight of a cationic polysaccharide and an effective amount of a sunscreen agent. These compositions are waterproof, freeze-thaw cycle stable, moisture retentive and exhibit unusual skin mildness properties.

9 Claims, No Drawings

WATERPROOF SUNBLOCK COMPOSITIONS

BACKGROUND OF THE INVENTION

1. Field of the Invention

The invention relates to an improved waterproof sunscreen composition.

2. The Related Art

Sunscreen formulations for use on human skin are well-known and many different types are commercially available to satisfy diverse consumer needs. For example, sunscreen formulations having different sun protection fact (SPF) values are available, thus allowing consumers to choose the amount of protection desired. SPF values range from zero upward with higher values indicating greater amounts of sun protection. SPF values of 2-4 indicate minimal sun protection, 4-6 indicate moderate sun protection, 8-15 indicate maximal sun protection and above 15 indicate ultra sun protection.

One important consideration when choosing a sunscreen is whether it resists coming off in water. Waterproof formulations can undergo about 80 minutes in water without significant SPF loss. The formulations can be especially desirable because they eliminate the need for reapplication after swimming, bathing or excessive perspiration.

A classical method of achieving waterproof properties is through the use of a hydrophobic resin. For instance, U.S. Pat. No. 4,897,259 (Murray et al) discloses success through use of copolymers of polyvinylpyrrolidone (PVP) and long alkyl chain olefins, commonly referred to as alkylated PVP's. Besides a sunscreen agent and the copolymer, a variety of other functional ingredients are incorporated including emulsifiers, two of which are stated to be phosphated esters and polyoxyethylene fatty ester phosphates.

Not only is it desirable for a sunscreen composition to be waterproof, but such compositions should desirably also impart certain skin feel advantages. Cationic emulsions which may provide skin performance advantages have been reported in U.S. Pat. No. 4,389,418 (Burton). Therein is disclosed a water-out emulsion containing petroleum or a mineral oil to moisturize the skin, a quaternary ammonium emulsifier, a fatty alcohol and a fatty ester emollient. Greaseless skin conditioning compositions based upon cationic polymers have also been reported in U.S. Pat. No. 4,438,095 (Grollier). Among the polymers disclosed are polyamines, polyaminoamides or quaternary polyammonium compounds. Emulsions are formed wherein the aqueous phase contains the cationic polymer and there are no detergent or foaming agents present.

Diquaternary nitrogen compounds have been reported in U.S. Pat. No. 4,886,890 (Chaudhuri et al) as useful in skin lotions and shampoos. These compositions may be formulated with a variety of detergents, such as sodium laureth-4 phosphate. Personal care products incorporating cationic polysaccharides have been described in U.S. Pat. No. 4,663,159 (Brode et al). Emulsifiers in the form of phosphate quaternary compounds have been disclosed in U.S. Pat. No. 4,209,449 and U.S. Pat. No. 4,503,002, each to Mayhew et al. These emulsifiers were said to be well tolerated by human tissue, exhibiting low irritation, and were stated to be suitable for use in cosmetics.

Skin moisture retention has been significantly increased by utilizing many of the cationic compounds mentioned in the above patents. Nonetheless, there remains considerable need for improvement in moisture retention. There are also the further problems of improving mildness and of providing stability against phase separation during freeze-thaw cycles.

Although there have been significant advances in the art of waterproofing sunscreen lotions and also improving their skin moisture retention properties, there still remains considerable need for improvements. For instance, it is desirable to formulate a composition not including any hydrophobic resins. These resins leave undesirable residues upon the skin and also give rise to stability problems. Stability against phase separation during freeze-thaw cycles is an important goal for formulators. Finally, there is also the need to reduce irritancy of the sunscreen products.

Accordingly, it is an object of the present invention to provide a sunscreen composition of the waterproof variety not requiring incorporation of a hydrophobic resin.

Another object of the present invention is to provide a sunscreen composition having improved skin moisture retention.

A further object of the present invention is to provide a sunscreen composition in aqueous emulsion form whose phases resist separation even under extended freeze-thaw cycling.

A still further object of the present invention is to provide a sunscreen composition having a relatively low human irritancy.

These and other objects of the present invention will more readily become apparent from the description and examples which follow.

SUMMARY OF THE INVENTION

A cosmetic composition is provided comprising:
(i) from about 0.10 to about 30% of a quaternary ammonium functionalized phosphate ester;
(ii) from about 0.10 to about 10% of a cationic polysaccharide; and
(iii) a sunscreen agent present in an effective amount to at least partially block ultraviolet radiation from reaching human skin upon which the composition is deposited.

The compositions of the present invention may either be oil-in-water or water-in-oil emulsions. Especially effective as the ester component are alkylamido quaternary ammonium phosphate esters. The cationic polysaccharide is especially effective when in the form of a cellulosic polymer quaternized with fatty alkyl groups.

DETAILED DESCRIPTION OF THE INVENTION

Now it has been discovered that a combination of a quaternary ammonium functionalized phosphate ester and a cationic polysaccharide can provide a sunscreen composition with excellent waterproof properties. Additionally, this composition demonstrates good moisture retention and excellent freeze-thaw stability.

A quaternary ammonium functionalized phosphate ester is a necessary first component of the compositions of this invention. The phosphate ester will conform to the following general formula:

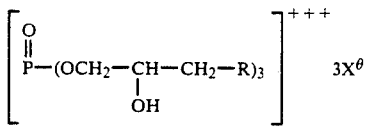

wherein R is a quaternary ammonium radical having from about 6 to about 40 carbons. This carbon atom limitation serves to include only materials of significant hydrophobic properties. The R radical can be cyclic or non-cyclic, aliphatic, aromatic or heterocyclic. X is an anion, such as halide, e.g., chloride.

In a preferred species, R is an amidoamine moiety of the formula:

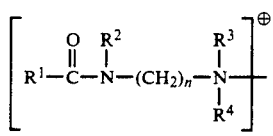

wherein

R is selected from the group consisting of alkyl, alkenyl, alkoxy and hydroxyalkyl having from 5 to 22 carbon atoms each, and from aryl and alkaryl having up to 20 carbon atoms;

$R^2$, $R^3$ and $R^4$ may each independently be selected from the group consisting of hydrogen, alkyl, hydroxyalkyl and alkenyl each having up to 6 carbon atoms, and from polyoxyalkylene of up carbon atoms;

$R^3$ and $R^4$ may additionally be selected from aceto and propriono groups and may even be taken together with the nitrogen to which they are attached so as to form a N-heterocyclic ring; and n is an integer from about 1 to 10.

In addition to the foregoing definitions where R is amidoamine, R may be a N-heterocyclic radical which may contain one additional hetero atom (e.g., oxygen or another nitrogen) and contains 5 to 6 total ring carbon atoms; optionally the heterocyclic radical may be substituted with alkyl and/or hydroxyalkyl of up to 20 carbon atoms each. Typical of such N-heterocyclic radicals are imidazolinyl, N-alkylmorpholino, alkylpyrimidino, alkyloxazolinyl, and the like. Such compounds may be represented by the formula:

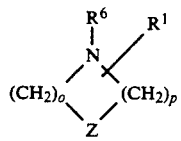

wherein

Z is N, S or O;

o is an integer from 0 to 3, p is an integer from 1 to 3, provided that the sum of o+p is from 3 to 4;

$R_1$ is a radical selected from the group consisting of alkyl, alkenyl, alkoxy and hydroxyalkyl units of from 2 to 22 carbon atoms each, and aryl and alkaryl of up to 20 carbon atoms; and $R^6$ is alkyl of from 2 to 6 carbon atoms which atoms may be substituted with a hydroxyl group.

Preferably R is derived from a tertiary amine radical of from about 10 to 40 carbon atoms. More preferred are tertiary amine radicals of the type ($C_6$-$C_{20}$ alkyl, di-methyl) amine such as N,N-dimethyl myristylamine, N,N-dimethyl-palmityl-amine, and N,N-dimethyl-laurylamine.

Of most interest, are the phosphate esters identified as Formulas I through III. These are commercially available from Mono Industries, Inc., Paterson, N.J., sold under the Monaquat designation.

MONAQUAT P-TC, P-TD, P-TS, PHOSPHOLIPID EFA

Formula I

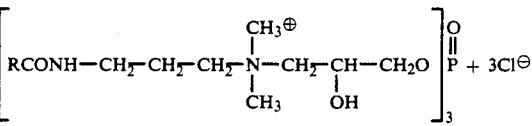

R = $C_5$-$C_{17}$ Alkyl

MONAQUAT P-TZ

Formula II

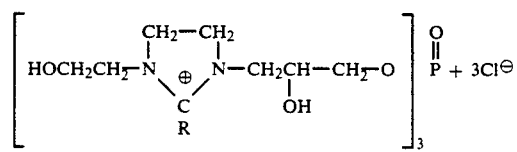

R = $C_5$-$C_{17}$ Alkyl

MONAQUAT P-TL

Formula III

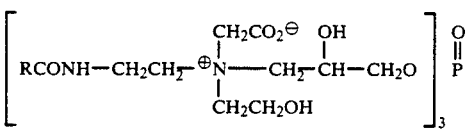

| Monaquat | Alkyl Group | % Active |
|---|---|---|
| P-TC | $C_5$-$C_{17}$ | 40.0 |
| P-TD | $C_{11}$-$C_{13}$ | 34.0 |
| P-TL | $C_{11}$-$C_{13}$ | 30.0 |
| P-TS | $C_{17}$ | 30.0 |
| P-TZ | $C_5$-$C_{17}$ | 30.0 |
| Phospholipid EFA | $C_{17}$ with 2 double bonds | 30.0 |

Most preferred from the above compounds are Monaquat P-TS, Monaquat P-TC, Monaquat P-TD and Phospholipid EFA.

Amounts of the quaternary phosphate ester will range from about 0.1 to about 30%, preferably from about 1 to about 15%, optimally between about 2 and 10% by weight of the composition.

A second essential component of the composition of this invention is a cationic polysaccharide. Polysaccharides of this invention are derived from naturally occurring polysaccharides or those modified by etherification, which are quaternized with a nitrogen-containing compound and alkylated with a compound, including a nitrogen-containing compound, containing a hydrophobe.

Polysaccharide starting materials include the naturally occurring, biosynthesized and derivatized carbohydrate polymers or mixtures thereof. Such materials encompass high molecular weight polymers composed of monosaccharide units joined by glycosidic bonds. These materials include the entire starch and cellulose families, pectin, chitosan; chitin; the seaweed products such as agar and carrageenan; alginate; the natural gums such as guar, arabic and tragacanth; bio-derived gums such as xanthan; and the like. Preferred starting materials include cellulosics conventionally employed for the preparation of cellulose ethers, such as chemical cotton, cotton linters, wood pulp, alkali cellulose, and the like and ether derivatives of the same. Such cellulose ethers include hydroxyethyl cellulose, hydroxypropyl cellulose, methyl cellulose, carboxymethyl cellulose, carboxyethyl cellulose, hydroxypropyl methyl cellulose, hydroxyethyl methyl cellulose, hydroxyethyl carboxymethyl cellulose, and the like. A particularly preferred polysaccharide starting material is hydroxyethyl cellulose. The polysaccharide starting material will possess a molecular weight corresponding to the number of polysaccharide repeat units, usually from 50 up to about 20,000. The molecular weight of the polysaccharides may be varied through controlled degradation procedures known in the art.

Etherified polysaccharides may be obtained commercially or produced from the polysaccharide starting materials mentioned previously. Etherification involves reacting pendent hydroxyl groups on the polysaccharide backbone with an etherifying agent, or mixtures thereof, which contain functional groups reactive with such hydroxyl groups. Etherification may be conducted to enhance the water-solubility of the polysaccharides, e.g. by ethoxylation. Typical etherifying agents include lower alkylating agents such as dimethyl sulfate, diethyl sulfate, methyl chloride, methyl bromide, ethyl chloride, ethyl bromide or n-propyl chloride; hydroxy alkylating agents such as ethylene oxide, propylene oxide or glycidol; and carboxy alkylating agents such as monochloroacetic acid, sodium chloroacetate or chloropropionic acid.

The polysaccharide starting materials are provided with quarternary nitrogen-containing substituents through quaternization reactions. Quaternization may be achieved by reacting the polysaccharides with quaternizing agents which are quaternary ammonium salts, including mixtures thereof, to effect substitution of the polysaccharide chain with quaternary nitrogen-containing groups. Typical quaternary ammonium salts which can be utilized include quaternary nitrogen-containing halides, halohydrins and epoxides. The quaternary ammonium salt may contain hydrophobes.

Particularly preferred are polymeric quaternary ammonium salts of hydroxyethyl cellulose reacted with a fatty alkyl dimethyl ammonium substituted epoxide. Illustrative preferred materials in this category are:

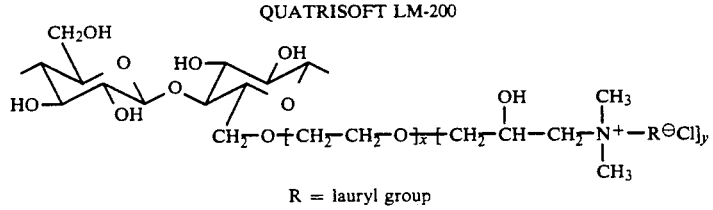

QUATRISOFT LM-200    Formula IV

R = lauryl group

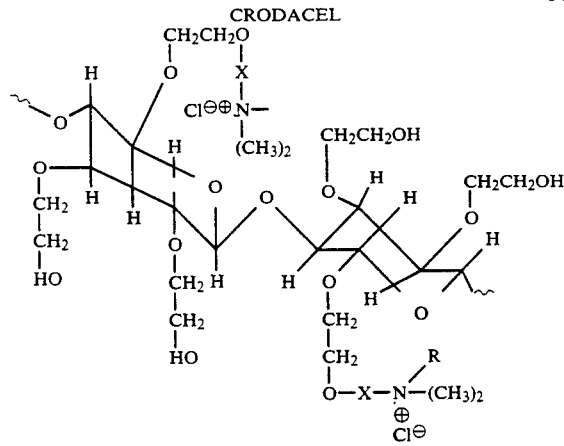

CRODACEL    Formula V

| Crodacel | Alkyl Group |
|---|---|
| QL | Lauryl |
| QM | Coco |
| QS | Stearyl |

Preferred R groups will have a chain length ranging from about 10 to about 20 carbon atoms in length. These materials are available from the Union Carbide Corporation under the trademark Quatrisoft LM-200 and from Croda, Inc. under the trademark Crodacel Q (L, M and S).

Amounts of the cationic polysaccharide will normally range from about 0.01 to about 10%, preferably from about 0.01 to about 5%, optimally between about 0.2 and 1% by weight of the compositions.

Although the invention is not limited to cosmetic compositions in the form of emulsions, a particularly suitable vehicle is that of an emulsion. By definition, an emulsion is a dispersed system containing at least two immiscible liquid phases, one of which is dispersed in the form of small droplets throughout the other. Water and oil are the most common immiscible liquid phases. An emulsion in which oil is dispersed as droplets throughout the aqueous phase is termed an oil-in-water emulsion. When water is the dispersed phase and an oil is the dispersion medium, a water-in-oil emulsion exists. Contemplated within the scope of this invention are emulsions in the forms of lotions and creams of both types of emulsions, those where the water phase is continuous and those where the oil phase is continuous. The amounts of these phases may range from about 99:1 to 1:99 by weight.

A sunscreen agent is a necessary third component of the compositions of this invention. The term "sunscreen agent" as used herein defines ultraviolet ray-blocking compounds exhibiting absorption within the wavelength region between 290 and 420 nm. Sunscreens may be classified into five groups based upon their chemical structure: para-amino benzoates; salicylates; cinnamates; benzophenones; and miscellaneous chemicals including menthyl anthralinate and digalloyl trioleate. Inorganic sunscreens may also be used including titanium dioxide, zinc oxide, iron oxide and polymer particles such as those of polyethylene and polyamides. Preferred materials include p-aminobenzoic acid and its derivatives, anthralinates; salicylates; cinnamates; courmarin derivatives; azoles; and tannic acid and its derivatives. Among FDA approved sunscreens are those listed in the table below.

|  | Approved % |
|---|---|
| UV-A Absorbers | |
| Oxybenzone. also known as 2-hydroxy-4-methoxy benzophenone, and benzophenone-3, available as Uvinul M-40 and Gafsorb 2H4M | 2-6 |
| Dioxybenzone, also known as 2,2 dihydroxy-4-methoxy benzophenone, and benzophenone-8 | 3 |
| Sulibenzone, also known as 2-hydroxy-4-methoxy benzophenone-5-sulphonic acid, and benzophenone-4, available as Uvinul MS-40 and Gafsorb 2H4MS | 5-10 |
| Menthyl anthralinate, also known as menthyl-o-aminobenzoate | 3.5-5 |
| UV-B Absorbers | |
| p-Amino benzoic acid, also known as PABA | 5-15 |
| Amyl dimethyl PABA (NA), also known as amyl-p-dimethyl ammonium benzoate, available as Padimate A | 1-5 |
| 2-Ethoxy ethyl p-methoxy cinnamate (NA), available as Cinoxate and Givtan-F | 1-3 |
| Diethanolamine p-ethoxy cinnamate, also known as DEA methoxy cinnamate, available as Parsol-Hydro | 8-10 |
| Digalloyl trioleate (NA), a component of Solprotex I | 2-5 |
| Ethyl-4-bis (hydroxypropyl) aminobenzoate, also known as ethyl dihydroxy propyl PABA, available as Amerscreen P | 1-5 |
| 2-Ethyl hexyl-2-cyano-3,3 diphenyl acrylate, also known as octocrylene and available as Uvinul N-539 | 7-10 |
| Ethyl hexyl p-methoxy cinnamate, also known as octyl methoxycinnamate available as Parsol MCX | 2-7.5 |
| 2-Ethyl hexyl salicylate, also known as octyl salicylate | 3-5 |
| Glyceryl aminobenzoate, also known as glyceryl p-aminobenzoate and glyceryl PABA, available as Escalol 106 | 2-3 |
| Homomenthyl salicylate, also known as 3,3,5-trimethylcyclohexyl salicylate | 4-15 |
| Lawsone with dihydroxyacetone (NA) | 0.25 with 33 |
| Octyl dimethyl PABA, also known as 2-ethyl hexyl p-dimethyl p-aminobenzoate, and 2-ethyl hexyl dimethyl PABA, available as Padimate O and Escalol 507 | 1.4-8 |
| 2-Phenyl benzimidazole 5-sulphoic acid | 1.4 |
| Triethanolamine salicylate | 5-12 |
| Physical Screens | |
| Red Petrolatum | 30-100 |

-continued

|  | Approved % |
|---|---|
| Titanium dioxide | 2-25 |

Although the quaternary ammonium functionalized phosphate esters are intended as the primary emulsifier and surfactant for systems of this invention, there may also be present nonionic emulsifiers. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono and di-fatty acid esters of ethylene glycol wherein the fatty acid moiety contains from 10 to 20 carbon atoms, fatty acid monoglyceride wherein the fatty acid moiety contains from 10 to 20 carbon atoms, diethylene glycol, polyethylene glycols of molecular weight 200 to 6000, propylene glycol of molecular weight 200 to 3000, sorbitol, sorbitan, polyoxyethylene sorbitol, polyoxyethylene sorbitan, and hydrophilic wax esters. Amounts of the nonionic emulsifier may range anywhere from about 0.1 to about 20% by weight of the emulsion, preferably from about 2 to about 10% by weight.

A variety of oily emollients may be employed in the compositions of this invention. These emollients may be selected from one or more of the following classes:

1. Hydrocarbon oils and waxes. Examples thereof are mineral oil, petroleum, paraffin, ceresin, ozokerite, microcrystalline wax, polyethylene, and perhydrosqualene.

2. Triglyceride esters such as vegetable and animal fats and oils. Examples include caster oil, cocoa butter, safflower oil, cottonseed oil, corn oil, olive oil, cod liver oil, almond oil, avocado oil, palm oil, sesame oil, squalane, and soybean oil.

3. Acetoglyceride esters, such as acetylated monoglycerides.

4. Ethoxylated glycerides, such as ethoxylated glyceryl monostearate.

5. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

6. Alkenyl esters of fatty acids having 10 to 20 carbon atoms. Examples thereof include oleyl myristate, oleyl stearate, and oleyl oleate.

7. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.

8. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecanyl alcohols are examples of satisfactory fatty alcohols.

9. Fatty alcohol ethers. Ethoxylated fatty alcohols of 10 to 20 carbon atoms including the lauryl, cetyl, stearyl, isostearyl, oleyl, and cholesterol alcohols, having attached thereto from 1 to 50 ethylene oxide groups or 1 to 50 propylene oxide groups.

10. Ether-esters such as fatty acid esters of ethoxylated fatty alcohols.

11. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

12. Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 mono- oleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters ar satisfactory polyhydric alcohol esters.

13. Wax esters such as beeswax, spermaceti, myristyl myristate, stearyl stearate.

14. Beeswax derivatives, e.g. polyoxyethylene sorbitol beeswax. These are reaction products of beeswax with ethoxylated sorbitol of varying ethylene oxide content, forming a mixture of ether esters.

15. Vegetable waxes including carnauba and candelilla waxes.

16. Phospholipids such as lecithin and derivatives.

17. Sterols. Cholesterol, cholesterol fatty acid esters are examples thereof.

18. Amides such as fatty acid amides, ethoxylated fatty acid amides, solid fatty acid alkanolamides.

Amounts of the above listed emollients may range anywhere from about 0.5 to about 40% by weight of the total composition. Preferably the amounts of these emollients will range from about 2 to about 25%, optimally between about 5 and 15% by weight.

Humectants of the polyhydric alcohol-type ma also be included in the compositions of this invention. The humectant aids in increasing the effectiveness of the emollient, reduces scaling, stimulates removal of built-up scale and improves skin feel. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerol. The amount of humectant may range anywhere from 0.5 to 20%, preferably between 1 and 15% by weight of the composition.

For improved lubricity, there may also be included one or more silicone oils or fluids which may be selected from a dimethyl polysiloxane, a methylphenyl polysiloxane and an alcohol-soluble silicone glycol copolymer. Preferred siloxanes include dimethyl polysiloxane (CTFA name dimethicone), a polysiloxane end- blocked with trimethyl units and polydimethylcyclosiloxane, (CTFA name cyclomethicone). The preferred siloxanes exhibit a viscosity from about 2 to 50 centistokes at 25° C. Amounts of the silicones can range up to 30% by weight of the compositions, preferably from about 1 to about 10% by weight.

The emulsions of the invention can also include thickeners/viscosifiers in amounts up to about 5% by weight of the composition. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses, and cross-linked acrylic acid polymers such as those sold by B. F. Goodrich under the Carbopol trademark.

Preservatives can desirably be incorporated into the cosmetic compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, imidazolidinyl urea, sodium dehydroxyacetate, propyl paraben and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Amounts of water in the composition may range anywhere from about 1 to about 99%, preferably from about 40 to about 90%, optimally between about 60 and 85% by weight.

Minor adjunct ingredients may also include fragrances, antifoam agents, bacteriostats, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

Sunscreen compositions of the present invention are described in Tables I II. In the first Table, common organic sunscreen agents, i.e. oxybenzone in combination with ethylhexyl p-methoxycinnamate, are incorporated as the sunscreen agent. Table II is formulated with an organic sunscreen agent, i.e. micronized titanium dioxide.

TABLE I

| Ingredients | Weight % |
|---|---|
| Cetyl Alcohol | 2.500 |
| Glycerol Monostearate (Kessco GMS) | 1.500 |
| Propyl Paraben | 0.100 |

TABLE I-continued

| Ingredients | Weight % | |
|---|---|---|
| Ethylhexyl p-methoxycinnamate (Parsol MCX) | 7.000 | Phase A |
| Oxybenzone (Uvinul M-40) | 3.000 | |
| Octyl Palmitate (Schercemol OP) | 2.000 | |
| Silicone Fluid | 1.000 | |
| Petroleum Jelly | 1.000 | |
| Deionized Water | 74.345 | Phase B |
| Glycerin USP | 4.000 | |
| Monaquat P-TS | 3.000 | |
| Antifoam AF | 0.005 | |
| Methyl Paraben | 0.150 | |
| Quatrisoft LM-200 | 0.250 | |
| Fragrance | 0.150 | |
| | 100.000 | |

TABLE II

| Ingredients | Weight % | |
|---|---|---|
| Cetyl Alcohol | 2.500 | Phase A |
| Glycerol Monostearate (Kessco GMS) | 1.500 | |
| Propyl Paraben | 0.100 | |
| Ethylhexyl p-methoxycinnamate (Parsol MCX) | 8.250 | |
| Micronized Titanium Dioxide | 3.000 | |
| Diisopropyl dimerate (Schercemol) | 2.000 | |
| Deionized Water | 75.245 | Phase B |
| Glycerin USP | 4.000 | |
| Monaquat P-TS | 3.000 | |
| Antifoam AF | 0.005 | |
| Methyl Paraben | 0.150 | |
| Quatrisoft LM-200 | 0.250 | |
| Fragrance | qs | |
| | 100.000 | |

EXAMPLE 2

Five member Sun Protection Factor (SPF) tests on human skin were performed on lotions incorporating sunscreen chemicals into the Monaquat P-Ts/Quatrisoft LM-200 formulas listed under Table I and II. These tests complied with the FDA monograph. Results of these tests are reported in Table III.

TABLE III

| No. | Ultraviolet Absorbers | SPF Before Swim | SPF After Swim |
|---|---|---|---|
| 1. | Ethylhexyl p-Methoxy Cinnamate Oxybenzone | 16.65 | 15.15 |
| 2. | Ethylhexyl p-Methoxy Cinnamate Micronized Titanium Dioxide | 17.14 | 16.44 |

Based on the results in Table III, it is evident that the experimental formulas retain a high measure of waterproof properties.

Although this invention has been described with reference to specific examples, it will be apparent to one skilled in the art that various modifications may be made thereto which fall within the scope and purview of the invention.

What is claimed is:

1. A cosmetic sunscreen composition which is waterproof comprising:
   (i) from about 0.10 to about 30% of a quaternary ammonium phosphate ester having the formula:

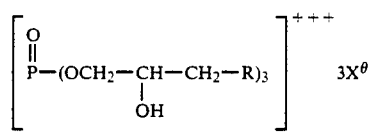

wherein R is a quaternary ammonium radical substituted with aliphatic radicals having from about 5 to about 40 carbon atoms; and X is an anion;
   (ii) from about 0.10 to about 10% of a cationic polysaccharide that is a hydroxyalkyl cellulose substituted with a quaternary ammonium group having at least one substituent attached thereto being an alkyl group of from 12 to 22 carbon atoms; and
   (iii) a sunscreen agent present in an effective amount to at least partially block ultraviolet radiation from reaching human skin upon which said composition is deposited, said sunscreen agent being selected from the group consisting of para-amino benzoates, salicylates, cinnamates, benzophenones, menthyl anthralinates, digalloyl trioleates, courmarins, azoles, tannic acids, inorganic pigments, polyethylene, polyamide and mixtures thereof.

2. A composition according to claim 1 wherein R is an amidoamine having the formula

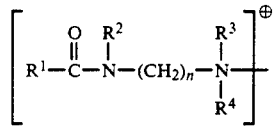

wherein
$R^1$ is selected from the group consisting of alkyl, alkenyl, alkoxy and hydroxyalkyl having from 5 to 22 carbon atoms each, and aryl and alkaryl having up to 20 carbon atoms;
$R^2$, $R^3$ and $R^4$ may each independently be selected from the group consisting of hydrogen, alkyl, hydroxyalkyl and alkenyl each having up to 6 carbon atoms, and polyoxyalkylene of up to 10 carbon atoms;
$R^3$ and $R^4$ may additionally be selected from the group consisting of aceto and propriono groups and may even be taken together with the nitrogen to which they are attached so as to form a N-heterocyclic ring, said ring containing from 5 to 6 total ring carbon atoms and represented by the formula:

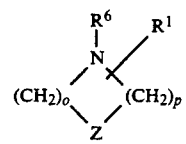

wherein
Z is N, S or O;
o is an integer from 0 to 3,
p is an integer from 1 to 3, provided that the sum of o+p is from 3 to 4;
$R^1$ is a radical selected from the group consisting of alkyl, alkenyl, alkoxy and hydroxyalkyl units of from 2 to 22 carbon atoms each, and aryl and alkaryl of up to 20 carbon atoms;

$R^6$ is alkyl of from 2 to 6 carbon atoms which atoms may be substituted with a hydroxyl group; and n is an integer from about 1 to 10.

3. A composition according to claim 1 wherein the alkyl is selected from the group consisting of lauryl, cocoly and stearyl.

4. A composition according to claim 1 wherein said phosphate ester is present in an amount from about 1 to about 5% by weight of the composition.

5. A composition according to claim 1 wherein said cationic polysaccharide is present in amount from about 0.2 to about 1% by weight of the composition.

6. A composition according to claim 1 wherein said phosphate ester is present as the main emulsifier and surfactant of the composition.

7. A composition according to claim 1 wherein said sunscreen agent is a substance having light absorption in the wavelength region between 290 and 420 nm.

8. A composition according to claim 1 wherein the sunscreen agent is selected from the group consisting of oxybenzone, dioxybenzone, sulibenzone, menthyl anthralinate, p-amino benzoic acid, amyl dimethyl p-aminobenzoate acid, 2-ethoxy ethyl p-methoxy cinnamate, diethanolamine p-ethoxy cinnamate, digalloyl trioleate, ethyl-4-bis (hydroxypropyl) aminobenzoate, 2-ethyl hexyl-2-cyano-3,3 diphenyl acrylate, ethyl hexyl p-methoxy cinnamate, 2-ethyl hexyl salicylate, glyceryl aminobenzoate, homomenthyl salicylate, dihydroxyacetone, octyl dimethyl p-aminobenzoic acid, 2-pheyl benzimidazole 5-sulphonic acid, triethanolamine salicylate, titanium dioxide, iron oxide, polyethylene, polyamide and mixtures thereof.

9. A cosmetic sunscreen composition which is waterproof comprising:

(i) from about 1 to about 5% of quaternary ammonium phosphate ester having the formula:

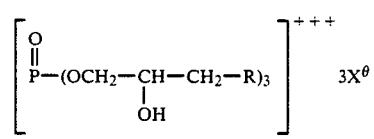

wherein R is a quaternary ammonium radical having from about 5 to about 40 carbon atoms; X is an anion; and R is an amidoamine having the formula:

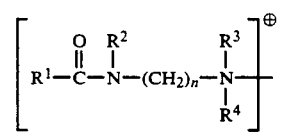

wherein $R^1$ is selected from the group consisting of alkyl, alkenyl, alkoxy and hydroxyalkyl having from 5 to 22 carbon atoms each, and aryl and alkaryl having up to 20 carbon atoms;

$R^2$, $R^3$ and $R^4$ may each independently be selected from the group consisting of hydrogen, alkyl, hydroxyalkyl and alkenyl each having up to 6 carbon atoms, and polyoxyalkylene of up to 10 carbon atoms;

$R^3$ and $R^4$ may additionally be selected from the group consisting of aceto and propriono groups; and n is an integer from about 1 to 10;

(ii) from about 0.10 to about 1% by weight of a cationic polysaccharide that is a hydroxyethyl cellulose substituted with a quaternary ammonium group having at least one substituent attached thereto being an alkyl group of from 12 to 22 carbon atoms; and (iii) a sunscreen agent present in an effective amount to at least partially block ultraviolet radiation from reaching human skin upon said composition is deposited, said sunscreen agent being selected from the group consisting of ethylhexyl p-methoxycinnamate, oxybenzone, titanium dioxide and combinations thereof.

* * * * *